(12) United States Patent
Burattin et al.

(10) Patent No.: US 7,105,696 B2
(45) Date of Patent: Sep. 12, 2006

(54) METHOD FOR MAKING NITRILE COMPOUNDS FROM ETHYLENICALLY UNSATURATED COMPOUNDS

(75) Inventors: Paolo Burattin, Lyons (FR); Alex Chamard, Corbas (FR); Jean-Christophe Galland, Lyons (FR)

(73) Assignee: Rhodia Polymide Intermediates, Saint Fons (FR)

( * ) Notice: Subject to any disclaimer, the term of this patent is extended or adjusted under 35 U.S.C. 154(b) by 233 days.

(21) Appl. No.: 10/250,477

(22) PCT Filed: Dec. 21, 2001

(86) PCT No.: PCT/FR01/04154

§ 371 (c)(1),
(2), (4) Date: Nov. 6, 2003

(87) PCT Pub. No.: WO02/053527

PCT Pub. Date: Jul. 11, 2002

(65) Prior Publication Data

US 2004/0063991 A1     Apr. 1, 2004

(30) Foreign Application Priority Data

Jan. 5, 2001  (FR) .................................. 01 00137

(51) Int. Cl.
*C07C 253/00* (2006.01)
(52) U.S. Cl. ........................ 558/338; 556/18; 502/155; 549/216
(58) Field of Classification Search .................. 556/18; 558/338; 502/155; 549/216
See application file for complete search history.

(56) References Cited

U.S. PATENT DOCUMENTS

| 3,739,011 A | 6/1973 | Drinkard |
| 5,981,772 A | 11/1999 | Foo et al. |
| 6,417,375 B1 * | 7/2002 | Mathey et al. ............... 549/216 |

FOREIGN PATENT DOCUMENTS

| FR | 2 778 915 | 11/1999 |
| FR | 2 787 446 | 6/2000 |
| WO | WO 98/22484 | 5/1998 |

OTHER PUBLICATIONS

V. Farina, "Large rate accelarations in the Stille reaction with tri-furylphosphine and trifurylarsine as palladium . . . ", *Journal of the American Chemical Society*, vol. 113, No. 25, 1991, pp. 9858-9595, XP002090428.

* cited by examiner

*Primary Examiner*—Kamal A. Saeed
*Assistant Examiner*—Robert Shiao
(74) *Attorney, Agent, or Firm*—Buchanan Ingersoll, P.C.

(57) ABSTRACT

The invention concerns a method for hydrocyanation of ethylenically unsaturated organic compounds comprising at least a nitrile function. The invention provides a method for hydrocyanation of an ethylenically unsaturated hydrocarbon compound by reacting in liquid medium the hydrogen cyanide in the presence of a catalyst comprising a metal element selected among transition metals and an organophosphorous ligand, characterised in that the organophosphorous ligand is a furylphosphine. The invention is in particular useful for synthesizing adiponitrile from butadiene.

20 Claims, No Drawings

METHOD FOR MAKING NITRILE COMPOUNDS FROM ETHYLENICALLY UNSATURATED COMPOUNDS

This invention relates to a process for hydrocyanation of ethylenically unsaturated organic compounds into compounds that comprise at least one nitrile function.

It relates more particularly to the hydrocyanation of diolefins such as butadiene or substituted olefins such as alkenenitriles such as pentene nitriles.

French Patent No. 1 599 761 describes a process for preparation of nitriles by the addition of hydrocyanic acid on organic compounds that have at least one double ethylene bond, in the presence of a catalyst with nickel and a triaryl phosphite. This reaction can be conducted with or without a solvent.

When a solvent is used in this process of the prior art, it is preferably a hydrocarbon, such as benzene or xylenes or a nitrile such as acetonitrile.

The catalyst used is an organic nickel complex, containing ligands such as phosphines, arsines, stibines, phosphites, arsenites or antimonites.

The presence of a promoter for activating the catalyst, such as a compound of boron or a metal salt, generally a Lewis acid, is also recommended in said patent.

Patent FR-A-2 338 253 proposed carrying out the hydrocyanation of compounds that have at least one unsaturated ethylene, in the presence of an aqueous solution of a compound of a transition metal, in particular nickel, palladium or iron, and a sulfonated phosphine.

The sulfonated phosphines that are described in this patent are sulfonated triarylphosphines and more particularly sulfonated triphenylphosphines.

This process makes possible a correct hydrocyanation, in particular of butadiene and pentene nitriles, an easy separation of the catalytic solution by simple decanting and consequently avoids as much as possible the rejection of effluents or waste containing the metals that are used as catalysts.

However, research is conducted to find new catalytic systems that provide a better performance both in catalytic activity and in stability.

One of the objects of this invention is to propose a new family of ligands that makes it possible to obtain with the transition metals catalytic systems that have an improved activity relative to the known systems.

For this purpose, this invention proposes a process for hydrocyanation of a hydrocarbon-containing compound that comprises at least one unsaturated ethylene by reaction in a liquid medium with hydrogen cyanide in the presence of a catalyst that comprises a metal element that is selected from among the transition metals and an organophosphorus ligand, characterized in that the organophosphorus ligand is a furylphosphine that corresponds to general formula (I) or to general formula (II):

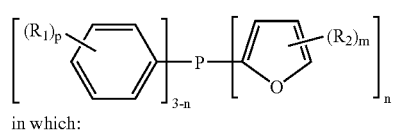

in which:

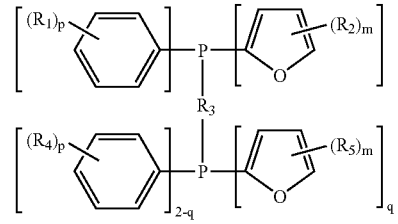

-continued n represents an integer from 1 to 3, q represents an integer that is equal to 1 or 2, radicals $R_1$, $R_2$, $R_4$, and $R_5$, identical or different, represent a hydrogen atom, a linear or branched alkyl radical that has 1 to 12 carbon atoms that can comprise heteroatoms, an aromatic or cycloaliphatic radical that may or may not be substituted and that can comprise heteroatoms, a carbonyl, alkoxycarbonyl or alkoxy radical, a halogen atom, a nitrile group or a haloalkyl group that has 1 to 12 carbon atoms, $R_3$ represents a covalent bond, a linear or branched aliphatic radical that can comprise heteroatoms, a radical that comprises an aromatic cycle or cycloaliphatic cycle that may or may not be substituted, or several aromatic cycles that are condensed or connected to one another by a covalent bond or by a radical that is formed by an oxygen atom, a sulfur atom or an alkyl radical, m, p represent an integer from 0 to 3.

According to a preferred characteristic of the invention, the metal element is selected from the group that comprises nickel, cobalt, iron, ruthenium, rhodium, palladium, osmium, iridium, platinum, copper, silver, gold, zinc, cadmium, and mercury.

According to the invention, the catalyst advantageously corresponds to general formula (III):

$$M[L_1]_t \quad (III)$$

in which:

M is a transition metal, $L_1$ represents the organophosphorus ligand of formula (I) or formula (II), t represents a number between 1 and 6 (inclusive).

As suitable compounds of general formulas (I) or (II), it is possible to cite the non-substituted trifurylphosphines that are described in an article by V. Farina and B. Krishnan published in Journal of American Chemical Society, 1991, 113, pages 9585–9595. Systems that comprise these trifurylphosphines exhibit a remarkable catalytic activity according to this article.

The furylphosphines of the invention are most often compounds of general formula (I) or (II) in which:

n represents an integer between 1 and 3 (inclusive).

For the preparation of furylphosphines according to general formulas (I) or (II), it is possible to refer to, for example, the article by A. J. Zapata and A. C. Rondon in Org. Prep. Proced. Int. 27, 5 (1995), pages 567 ff.

The furylphosphines make it possible to prepare organometallic complexes that comprise at least one furylphosphine of formula (I) or formula (II) and at least one metal.

The metals that can be complexed by the furylphosphines are generally all the transition metals of groups 1b, 2b, 3b, 4b, 5b, 6b, 7b and 8 of the periodic table, as published in "Handbook of Chemistry and Physics, 51st Edition (1970–1971)" of The Chemical Rubber Company.

Among these metals, it is possible to cite more particularly the metals that can be used as catalysts of hydrocyanation reactions. Thus, it is possible to mention by way of nonlimiting examples nickel, cobalt, iron, ruthenium, rhodium, palladium, osmium, iridium, platinum, copper, silver, gold, zinc, cadmium, and mercury.

The preparation of the organometallic complexes that comprise the furylphosphines can be carried out by bringing into contact a solution of a compound of the metal that is selected with a solution of the furylphosphine of formula (I) or (II).

The compound of the metal can be dissolved in a solvent.

The metal can be found in the compound that is used, either to the degree of oxidation that it will have in the organometallic complex, or to a higher degree of oxidation.

By way of example, it is possible to indicate that in the organometallic complexes of the invention, rhodium is of degree of oxidation (I), ruthenium is of degree of oxidation (II), platinum is of degree of oxidation (O), palladium is of degree of oxidation (O), osmium is of degree of oxidation (II), iridium is of degree of oxidation (I), and nickel is of degree of oxidation (O).

If, during the preparation of the organometallic complex, the metal is used at a higher degree of oxidation, it can be reduced in situ.

The organometallic complexes that comprise the furylphosphines of formula (I) or (II) can be used as catalysts in the hydrocyanation reactions of olefins.

As a transition metal, the compounds of the transition metals, more particularly the compounds of nickel, palladium, iron or copper, are preferably used.

Among the above-mentioned compounds, the most preferred compounds are those of nickel.

It is possible to cite by way of nonlimiting examples:
the compounds in which nickel is of degree of oxidation zero like potassium tetracyanonickelate $K_4[Ni(CN)_4]$, bis(acrylonitrile)nickel is of degree of oxidation zero, bis(cyclooctadiene-1,5)nickel (also called $Ni(cod)_2$) and the derivatives that contain ligands such as tretrakis (triphenyl phosphine)nickel is of degree of oxidation zero.
the compounds of nickel such as the carboxylates (in particular acetate), carbonate, bicarbonate, borate, bromide, chloride, citrate, thiocyanate, cyanide, formate, hydroxide, hydrophosphite, phosphite, phosphate and derivatives, iodide, nitrate, sulfate, sulfite, aryl- and alkyl-sulfonates.

When the compound of nickel that is used corresponds to an oxidation state of the nickel that is higher than 0, a nickel reducing agent that reacts preferably with the latter under the conditions of the reaction is added to the reaction medium. This reducing agent can be organic or mineral. It is possible to cite as nonlimiting examples the borohydrides such as $BH_4Na$, $BH_4K$, the Zn powder, magnesium or hydrogen.

When the nickel compound that is used corresponds to the oxidation state O of nickel, it is also possible to add a reducing agent such as those mentioned above, but this addition is not imperative.

When an iron compound is used, the same reducing agents are suitable.

In the case of palladium, the reducing agents can also be elements of the reaction medium (phosphine, solvent, olefin).

The organic compounds that comprise at least one double ethylene bond that is used more particularly in this process are the diolefins such as butadiene, isoprene, hexadiene-1,5, cyclooctadiene-1,5, ethylenically unsaturated aliphatic nitriles, particularly the linear pentene nitriles such as pentene-3-nitrile, pentene-4-nitrile, the monoolefins such as styrene, methyl styrene, vinylnaphthalene, cyclohexene, methyl-cyclohexene as well as the mixtures of several of these compounds.

The pentene nitriles in particular can contain amounts, generally in the minority, of other compounds, such as methyl-2-butene-3-nitrile, methyl-2-butene-2-nitrile, pentene-2-nitrile, valeronitrile, adiponitrile, methyl-2-glutaronitrile, ethyl-2-succinonitrile or butadiene, obtained, for example, from the prior reaction of hydrocyanation of butadiene into unsaturated nitriles.

Actually, during the hydrocyanation of butadiene, non-negligible amounts of methyl-2butene-3-nitrile and methyl-2-butene-2-nitrile are formed with the linear pentene nitriles.

The catalytic system that is used for the hydrocyanation according to the process of the invention can be prepared before its introduction into the reaction zone, for example by the addition to the phosphine of formula (I) or (II) alone or dissolved in a solvent, the suitable amount of compound of the transition metal selected and optionally reducing agent. It is also possible to prepare the catalytic system "in situ" by simple addition of phosphine and the transition metal compound in the hydrocyanation reaction medium before or after the addition of the compound to be hydrocyanated.

The amount of compound of the nickel or another transition metal that is used is selected to obtain a molar concentration of transition metal per mol of organic compounds to be hydrocyanated or isomerized of between $10^{-4}$ and 1, and preferably of between 0.005 and 0.5 mol of nickel or another transition metal that is used.

The amount of phosphine of formula (I) or (II) that is used to form the catalyst is selected such that the number of moles of this compound relative to 1 mol of transition metal is 0.5 to 500 and preferably 2 to 100.

Although the reaction is generally conducted without solvent, it may be advantageous to add an inert organic solvent. The solvent may be a solvent of the catalyst that is miscible with the phase that comprises the compound to be hydrocyanated at the hydrocyanation temperature. By way of examples of such solvents, it is possible to cite the aromatic, aliphatic or cycloaliphatic hydrocarbons.

The hydrocyanation reaction is generally carried out at a temperature of 10° C. to 200° C. and preferably of 30° C. to 120° C. It can be carried out in a one-phase medium.

The process of the invention can be used continuously or intermittently.

The hydrogen cyanide that is used can be prepared from metal cyanides, in particular sodium cyanide, or cyanohydrins, such as the cyanohydrin of acetone or by any other known synthesis process.

The hydrogen cyanide is introduced into the reactor in gaseous form or in liquid form. It can also first be dissolved in an organic solvent.

Within the framework of intermittent use, it is possible in practice to load into a reactor, purged in advance with a cover gas (such as nitrogen, argon), either a solution that contains all or a portion of the various components such as furylphosphine, the transition metal compound, the optional reducing agent and solvent, or said components separately. Generally, the reactor is then brought to the selected temperature, then the compound to be hydrocyanated is introduced. The hydrogen cyanide is then itself introduced, preferably continuously and uniformly.

When the reaction (whose evolution can be followed by metering of samples) is ended, the reaction mixture is drawn off after cooling, and the products of the reaction are isolated, for example, by distillation.

An improvement to the hydrocyanation process of ethylenically unsaturated compounds according to this invention relates in particular to the hydrocyanation of said ethylenically unsaturated nitrile compounds by reaction with the hydrogen cyanide and consists in using a catalytic system according to this invention with a co-catalyst that consists of at least one Lewis acid.

The ethylenically unsaturated compounds that can be used in this improvement are generally those that have been cited for the basic process. It is more particularly advantageous, however, to apply it to the reaction for hydrocyanation into dinitriles of ethylenically unsaturated aliphatic nitriles, in particular to linear pentene nitriles such as pentene-3-nitrile, pentene-4nitrile and mixtures thereof.

These pentene nitriles can contain amounts, generally in a minority, of other compounds, such as methyl-2-butene-3-nitrile, methyl-2-butene-2-nitrile, pentene-2-nitrile, valeronitrile, adiponitrile, methyl-2-glutaronitrile, ethyl-2-succinonitrile or butadiene, obtained from the prior reaction of hydrocyanation of butadiene and/or the isomerization of methyl-2-butene-3-nitrile into pentene nitriles.

The Lewis acid that is used as a co-catalyst makes it possible in particular, in the case of the hydrocyanation of the ethylenically unsaturated aliphatic nitriles, to improve the linearity of dinitriles that are obtained, i.e., the percentage of linear dinitrile relative to the total quantity of dinitriles that are formed, and/or to increase the activity and the service life of the catalyst.

Lewis acid is defined in this text according to the usual concept of electron doublet acceptor compounds.

It is possible to use in particular the Lewis acids that are cited in the work that is edited by G. A. OLAH "Friedel-Crafts and Related Reactions," Tome 1, pages 191–197 (1963).

The Lewis acids that can be used as co-catalysts in this process are selected from among the compounds of the elements of groups Ib, IIb, IIIa, IIIb, IVa, IVb, Va, Vb, VIb, VIIb and VIII of the periodic table. These compounds are most often salts, in particular halides, such as chlorides or bromides, sulfates, sulfonates, halosulfonates, perhaloalkyl sulfonates, in particular fluoroalkyl sulfonates or perfluoroalkyl sulfonates, carboxylates and phosphates.

By way of nonlimiting examples of such Lewis acids, it is possible to cite zinc chloride, zinc bromide, zinc iodide, manganese chloride, manganese bromide, cadmium chloride, cadmium bromide, stannous chloride, stannous bromide, stannous sulfate, stannous tartrate, indium trifluoromethyl sulfonate, the chlorides or bromides of elements of rare earths such as lanthanum, cerium, praseodymium, neodymium, samarium, europium, gadolinium, terbium, dysprosium, hafnium, erbium, thallium, ytterbium and lutetium, cobalt chloride, ferrous chloride and yttrium chloride.

It is also possible to use as Lewis acid organometallic compounds such as triphenylborane, and titanium isoproylate. Of course, it is possible to use mixtures of several Lewis acids.

Among the Lewis acids, most particularly zinc chloride, zinc bromide, stannous chloride, stannous bromide, triphenylborane and the chloride mixtures of stannous zinc/chloride are preferred.

The Lewis acid co-catalyst that is used generally represents from 0.01 to 50 mol per mol of transition metal compound, more particularly nickel compound, and preferably 1 to 10 mol per mol.

As for the use of the basic process of the invention, the catalytic solution that is used for the hydrocyanation in the presence of Lewis acid can be prepared before its introduction into the reaction zone, for example by addition to the reaction medium of the phosphine of formula (I) or (II) of the suitable amount of compound of the selected transition metal, of Lewis acid, and optionally of reducing agent. It is also possible to prepare the "in-situ" catalytic solution by simple mixing of these various components.

It is also possible under the conditions of the hydrocyanation process of this invention, and in particular in operating in the presence of the catalyst that is described above that comprises at least one furylphosphine of formula (I) or (II) and at least one compound of a transition metal, to carry out, in the absence of hydrogen cyanide, the isomerization of methyl-2butene-3-nitrile into pentene nitriles, and more generally branched unsaturated nitriles into linear unsaturated nitriles.

The methyl-2-butene-3-nitrile that is subjected to isomerization according to the invention can be used alone or mixed with other compounds.

Methyl-2-butene-3-nitrile can thus be inserted in a mixture with methyl-2-butene-2nitrile, pentene-4-nitrile, pentene-3-nitrile, pentene-2-nitrile, butadiene, adiponitrile, methyl-2glutaroronitrile, ethyl-2-succinonitrile or valeronitrile.

It is particularly advantageous to treat the reaction mixture that is obtained from the hydrocyanation of butadiene by HCN in the presence of at least one furylphosphine of formula (I) or (II) and at least one compound of a transition metal, more preferably a nickel compound of degree of oxidation 0, as defined above.

Within the scope of this preferred variant, whereby the catalytic system was already present for the hydrocyanation reaction of the butadiene, it is enough to halt all introduction of hydrogen cyanide to allow the isomerization reaction to occur.

It is possible, if necessary, in this variant to lightly flush the reactor with a cover gas such as nitrogen or argon, for example, to expel the hydrocyanic acid that could still be present.

The isomerization reaction is generally carried out at a temperature of 10° C. to 200° C. and preferably of 60° C. to 120° C.

In the preferred case of an isomerization that immediately follows the reaction for hydrocyanation of butadiene, it will be advantageous to operate at the temperature at which the hydrocyanation has been conducted.

As for the hydrocyanation process of ethylenically unsaturated compounds, the catalytic system that is used for the isomerization can be prepared before its introduction into the reaction zone, for example by the addition into the reaction medium of the furylphosphine of formula (I) or (II) of the suitable amount of transition metal compound that is selected and optionally reducing agent. It is also possible to prepare the "in-situ" catalytic system by simple mixing of these various components. The amount of transition metal compound and more particularly the nickel that is used, as well as the amount of furylphosphine of formula (I) or (II) are the same as for the hydrocyanation reaction.

Although the isomerization reaction is generally conducted without solvent, it may be advantageous to add an inert organic solvent that can be that of subsequent extraction. This is the case in particular when such a solvent was used in the reaction for hydrocyanation of butadiene that was used in preparing the medium subjected to the isomerization reaction. Such solvents can be selected from among those that were cited above for the hydrocyanation.

However, the preparation of dinitrile compounds by hydrocyanation of an olefin such as butadiene can be carried out by using a catalytic system according to the invention for the stages for formation of unsaturated nitriles and the isomerization stage above, whereby the reaction for hydrocyanation of unsaturated nitriles into dinitriles can be used with a catalytic system according to the invention or any other catalytic system that is already known for this reaction.

Likewise, the reaction for hydrocyanation of the olefin into unsaturated nitriles and the isomerization of the latter can be carried out with a catalytic system that is different from that of the invention, whereby the stage for hydrocyanation of the unsaturated nitriles into dinitriles was used with a catalytic system according to the invention.

The following examples illustrate the invention.

In the example, the abbreviations that are used have the meanings that are indicated below.

| | |
|---|---|
| cod: | 1,5-cyclooctadiene. |
| eq: | equivalent. |
| 2M3BN: | 2-methyl-3-butenenitrile. |
| 2M2BN: | 2-methyl-2-butenenitrile. |
| 3PN: | 3-pentene nitrile. |
| 4PN: | 4-pentene nitrile. |
| 3 + 4PN: | 3PN + 4PN. |
| TT (Y): | Rate of transformation of the product to be hydrocyanated Y that corresponds to the ratio of the number of transformed moles of Y to the number of initial moles of Y. |
| RR (X): | Actual yield of compound X that corresponds to the ratio of the number of formed moles of X to the number of maximum moles of X. |
| RT (X): | Selectivity of compound X that corresponds to the ratio of RR (X) to TT (Y). |
| CPG: | Gas phase chromatography. |
| ml: | milliliter |
| mol: | mole. |
| mmol: | millimol. |

In the tests below, the products used are:

a composition that comprises 2M3BN and other products. The molar formulation of this composition is given in Table 1 below.

TABLE 1

| Component | Abbreviation | Mol % |
|---|---|---|
| 2-Methyl-3-butenenitrile | 2M3BN | 77.89 |
| trans-2-Methyl-2-butenenitrile | T2M2BN | 11.81 |
| 2-Methylbutyronitrile | 2MBN | 0.03 |
| cis-2-Pentene nitrile | C2PN | 5.12 |
| 4-Vinylcyclohexene | 4VCH | 0.08 |
| cis-2-Methyl-2-butenenitrile | C2M2BN | 0.24 |
| 4-Pentene nitrile | 4PN | 0.04 |
| trans-3-Pentene nitrile | T3PN | 4.69 |
| trans-2-Pentene nitrile | T2PN | 0.07 |
| cis-3-Pentene nitrile | C3PN | 0.05 | ligands defined in Table II below:

TABLE II

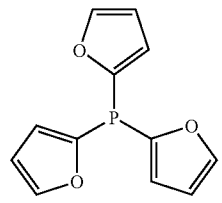

Tris(2-furyl)phosphine
Ligand A

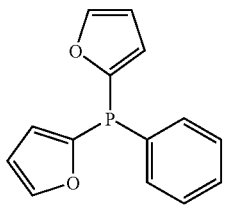

Bis(2-furyl)phenylphosphine
Ligand B

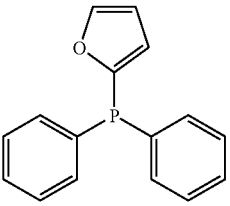

(2-furyl)diphenylphosphine
Ligand C

The tests were carried out according to the following operating procedure:

In a pill machine that is equipped with a magnetized bar and under argon, the following are loaded: 20 mg (0.073 mmol; M 275 g/mol; 1.0 equivalent) of $Ni(cod)_2$ and 5.0 equivalents of ligand A, B or C. About 1 ml (810 mg; d=0.81; M=81.12 g/mol) of degassed and anhydrous 2M3BN is added. The mixture is stirred at 100° C. in a closed system for 1 hour, then cooled at ambient temperature. The concentrations of different products are determined by analysis by GPC of the reaction medium.

The results that are obtained are summarized in Table III below:

TABLE III

| Example | Ligand | TT (2M3BN) | RT (3 + 4PN) | RT (2M2BN) |
|---|---|---|---|---|
| 1 | Ligand A | 32% | 89% | 3% |
| 2 | Ligand B | 72% | 92% | 1% |
| 3 | Ligand C | 81% | 91% | 5% |

EXAMPLE 4

Hydrocyanation of 3-PN into ADN

Under an argon atmosphere, the reagents are loaded into a 60 ml Schott tube in the following order: 3-pentene nitrile (6 mmol), dimethylformamide (2.15 g), trifurylphosphine (1 mmol), Ni(cod)$_2$ (0.2 mmol), and indium triflate (0.2 mmol). The mixture is stirred and brought to a temperature of 65° C.

The hydrocyanic acid (6 mmol) is introduced at 2 hours 55 minutes. The temperature is kept at 65° C. for 5 minutes after the end of the addition.

The reaction mass is then cooled to ambient temperature (20° C.), diluted with acetone then degassed with nitrogen.

The reaction mass is analyzed by gas phase chromatography.

The yield of adiponitrile relative to the pentene-3-nitrile that is input is equal to 14%, and the molar ratio between adiponitrile and the total quantity of dinitriles is 82%.

EXAMPLE 5

Hydrocyanation of 3-PN into ADN

In a glove compartment, under an argon atmosphere, the reagents are loaded into a 60 ml Schott tube in the following order: 3-pentene nitrile (6 mmol), dimethylformamide (2.15 mg), difurylphenylphosphine (1 mmol), nickelcyclooctadiene (0.2 mmol), indium triflate (0.2 mmol), and cyanohydrin (6 mmol). The tube is plugged by a septum. The reaction mass is homogenized by manual stirring and then heated to 65° C. for two hours.

The reaction mass is then cooled to ambient temperature, diluted with acetone and then degassed.

The reaction mass is analyzed by gas-phase chromatography.

The adiponitrile yield relative to the pentene-3-nitrile that is input is equal to 8%, and the molar ratio between adiponitrile and the total quantity of dinitriles is 83%.

EXAMPLE 6

Hydrocyanation of 3-PN into ADN

The reaction mass is then cooled to ambient temperature, diluted with acetone and then degassed.

The reaction mass is analyzed by gas phase chromatography.

Under an argon atmosphere, in a 60 ml Schott-type glass tube that is equipped with a septum plug, the following are loaded in the following sequence: ligand A (2.7 mmol, 5 equivalents), 1.7 ml (16.1 mmol; 30 equivalents) of anhydrous 3PN, 148 mg (0.54 mmol; 1 equivalent) of Ni(cod)$_2$ and Lewis acid, hafnium tetrachloride (0.54 mmol; 1 equivalent). The mixture is brought to 70° C. while being stirred. The acetone cyanohydrin is injected into the reaction medium by an infusion pump at a flow rate of 0.45 ml per hour. After 3 hours of injection, the infusion pump is halted. The mixture is brought to ambient temperature, diluted with acetone and analyzed by gas phase chromatography.

The yield of dinitrile compounds relative to the pentene-3-nitrile that is input is equal to 24%, and the molar ratio between adiponitrile and the total quantity of dinitriles is 80%.

EXAMPLE 7

Hydrocyanation of 3-PN into ADN

The reaction mass is then cooled to ambient temperature, diluted with acetone and then degassed.

The reaction mass is analyzed by gas phase chromatography,

Under an argon atmosphere, in a 60 ml Schott-type glass tube that is equipped with a septum plug, the following are loaded in the following sequence: ligand A (2.7 mmol, 5 equivalents), 1.7 ml (16.1 mmol; 30 equivalents) of anhydrous 3PN, 148 mg (0.54 mmol; 1 equivalent) of Ni(cod)$_2$, and Lewis acid, yttrium triflate (0.54 mmol; 1 equivalent). The mixture is brought to 70° C. while being stirred. The cyanohydrin of the acetone is injected into the reaction medium by an infusion pump at a flow rate of 0.45 ml per hour. After 3 hours of injection, the infusion pump is halted. The mixture is brought to ambient temperature, diluted with acetone and analyzed by gas phase chromatography.

The yield of dinitrile compounds relative to the pentene-3-nitrile that is input is equal to 39%, and the molar ratio between adiponitrile and the total quantity of dinitriles is 85%.

EXAMPLE 8

Hydrocyanation of 3-PN into ADN

The reaction mixture is then cooled to ambient temperature, and diluted with acetone and then degassed.

The reaction mass is analyzed by gas phase chromatography.

Under an argon atmosphere, in a 60 ml Schott-type glass tube that is equipped with a septum plug, the following are loaded in the following sequence: ligand A (2.7 mmol, 5 equivalents), 1.7 ml (16.1 mmol; 30 equivalents) of anhydrous 3PN, 148 mg (0.54 mmol; 1 equivalent) of Ni(cod)$_2$ and the Lewis acid, tin triflate (0.54 mmol; 1 equivalent). The mixture is brought to 70° C. while being stirred. The cyanohydrin of the acetone is injected into the reaction medium by an infusion pump at a flow rate of 0.45 ml per hour. After 3 hours of injection, the infusion pump is halted. The mixture is brought to ambient temperature, diluted with acetone and analyzed by gas phase chromatography.

The yield of dinitrile compounds relative to the pentene-3-nitrile that is input is equal to 22%, and the molar ratio between adiponitrile and the total quantity of dinitriles is 84%.

EXAMPLE 9

Hydrocyanation of 3-PN into ADN

The reaction mass is then cooled to ambient temperature, diluted with acetone and then degassed.

The reaction mass is analyzed by gas phase chromatography.

Under an argon atmosphere, in a 60 Schott-type glass tube that is equipped with a septum plug, the following are loaded in the following sequence: ligand B (2.7 mmol, 5 equivalents), 1.7 ml (16.1 mmol; 30 equivalents) of anhydrous 3PN, 148 mg (0.54 mmol; 1 equivalent) of Ni(cod)$_2$ and the Lewis acid, boron triphenyl (0.54 mmol; 1 equivalent). The mixture is brought to 70° C. while being stirred. The cyanohydrin of the acetone is injected into the reaction medium by an infusion pump at a flow rate of 0.45 ml per hour. After 3 hours of injection, the infusion pump is halted. The mixture is brought to ambient temperature, diluted with acetone and analyzed by gas phase chromatography.

The yield of dinitrile compounds relative to the pentene-3-nitrile that is input is equal to 5%, and the molar ratio between adiponitrile and the total quantity of dinitriles is 83%.

EXAMPLE 10

Hydrocyanation of 3-PN into ADN

The reaction mass is then cooled to ambient temperature, diluted with acetone and then degassed.

The reaction mass is analyzed by gas phase chromatography.

Under an argon atmosphere, in a 60 ml Schott-type glass tube that is equipped with a septum plug, the following are loaded in the following sequence: ligand C (2.7 mmol, 5 equivalents), 1.7 ml (16.1 mmol; 30 equivalents) of anhydrous 3PN, 148 mg (0.54 mmol; 1 equivalent) of Ni(cod)$_2$ and the Lewis acid, zinc chloride (0.54 mmol; 1 equivalent). The mixture is brought to 70° C. while being stirred. The cyanohydrin of the acetone is injected into the reaction medium by an infusion pump at a flow rate of 0.45 ml per hour. After 3 hours of injection, the infusion pump is halted. The mixture is brought to ambient temperature, diluted with acetone and analyzed by gas phase chromatography.

The yield of dinitrile compounds relative to the pentene-3-nitrile that is input is equal to 42%, and the molar ratio between adiponitrile and the total quantity of dinitriles is 58%.

The invention claimed is:

1. A process of hydrocyanation of a hydrocarbon-containing ethylenically unsaturated compound that comprises reaction of said compound in a liquid medium with hydrogen cyanide in the presence of a catalyst that comprises a compound comprising at least one transition metal and at least one organophosphorus ligand, wherein the organophosphorus ligand is a furylphosphine that corresponds to general formula (I) or (II):

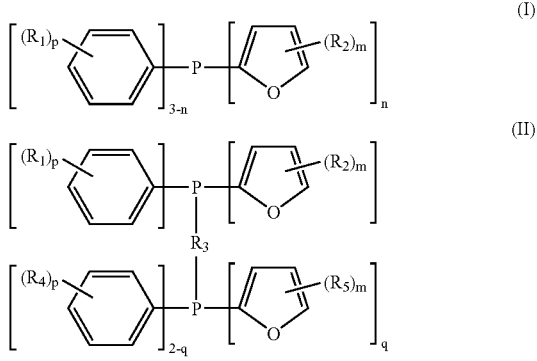

in which:

n represents an integer from 1 to 3, q represents an integer equal to 1 or 2, radicals $R_1$, $R_2$, $R_4$, and $R_5$, identical or different, represent a hydrogen atom, a linear or branched alkyl radical that has 1 to 12 carbon atoms that optionally includes heteroatoms, an optionally substituted aromatic or cycloaliphatic radical that optionally includes heteroatoms, a carbonyl, alkoxycarbonyl or alkoxy radical, a halogen atom, a nitrile group or a haloalkyl group that has 1 to 12 carbon atoms, $R_3$ represents a covalent bond, a linear or branched aliphatic radical that optionally includes heteroatoms, a radical that comprises an optionally substituted aromatic cycle or cycloaliphatic cycle, or several aromatic cycles that are condensed or connected to one another by a covalent bond or by a radical that is formed by an oxygen atom, a sulfur atom or an alkyl radical, and m, p represent an integer from 0 to 3.

2. Process according to claim 1, wherein the transition metal is selected from the group consisting of nickel, cobalt, iron, ruthenium, rhodium, palladium, osmium, iridium, platinum, copper, silver, gold, zinc, cadmium, and mercury.

3. Process according to claim 1, wherein the reaction is carried out in a one-phase medium.

4. Process according to claim 1, wherein the catalyst corresponds to general formula (III):

in which:

M is a transition metal, $L_1$ represents the organophosphorus ligand of formula (I), t represents a number between 1 and 6 (inclusive).

5. Process according to claim 1, wherein the reaction medium comprises a solvent of the catalyst that is miscible with the phase that comprises the compound to be hydrocyanated at the hydrocyanation temperature.

6. Process according to claim 1, wherein the compounds of the transition metals are those of nickel and are selected from the group consisting of:

the compounds in which nickel has a degree of oxidation of zero;

the compounds of nickel selected from the group consisting of carboxylates, carbonate, bicarbonate, borate, bromide, chloride, citrate, thiocyanate, cyanide, formate, hydroxide, hydrophosphite, phosphite, phosphate and derivatives, iodide, nitrate, sulfate, sulfite, aryl- and alkyl-sulfonates.

7. Process according to claim 1, wherein the ethylenically unsaturated compound is selected from the group consisting of butadiene, isoprene, hexadiene-1,5, cyclooctadiene-1,5, ethylenically unsaturated aliphatic nitriles, monoolefins, vinylnaphthalene, cyclohexene, methyl-cyclohexene and mixtures of these compounds.

8. Process according to claim 1, wherein the amount of transition metal is selected such that per mol of compound to be hydrocyanated, there is between $10_{-4}$ and 1 mol of the transition metal that is used and wherein the amount of furylphosphine of formula (I) or formula (II) that is used is selected such that the number of moles of this compound relative to 1 mol of transition metal is 0.5 to 500.

9. Process according to claim 1, wherein the hydrocyanation reaction is carried out at a temperature of 10° C. to 200° C.

10. Process according to claim 1, wherein the process is performed in the presence of a catalytic system that comprises at least one compound of a transition metal, at least one furylphosphine of formula (I) or (II) and a co-catalyst that consists of at least one Lewis acid.

11. Process according to claim 10, wherein the ethylenically unsaturated compound is selected from the group consisting of ethylenically unsaturated aliphatic nitriles and mixtures thereof.

12. Process according to claim 11, wherein the aliphatic nitriles and mixtures thereof comprise linear pentene nitriles that contain other compounds selected from the group consisting of methyl-2-butene-3-nitrile, methyl-2-butene-2-nitrile, pentene-2-nitrile, valeronitrile, adiponitrile, methyl-2-glutaronitrile, ethyl-2-succinonitrile and butadiene.

13. Process according to claim 10, wherein the Lewis acid that is used as a co-catalyst is selected from the group consisting of elements of groups Ib, IIb, IIIa, IIIb, IVa, IVb, Va, Vb, VIb, VIIb and VIII of the periodic table.

14. Process according to claim 10, wherein the Lewis acid comprises a salt selected from the group consisting of halides, sulfates, sulfonates, haloalkyl sulfonates, perhaloalkyl sulfonates, carboxylates and phosphates.

15. Process according to claim 10, wherein the Lewis acid is selected from the group consisting of zinc chloride, zinc bromide, zinc iodide, manganese chloride, manganese bromide, cadmium chloride, cadmium bromide, stannous chloride, stannous bromide, stannous sulfate, stannous tartrate, indium trifluoromethyl sulfonate, the chlorides or bromides of elements of rare earths such as lanthanum, cerium, praseodymium, neodymium, samarium, europium, gadolinium, terbium, dysprosium, hafnium, erbium, thallium, ytterbium and lutetium, cobalt chloride, ferrous chloride, yttrium chloride and mixtures thereof, and organometallic compounds.

16. Process according to claim 10, wherein the Lewis acid that is used represents 0.01 to 50 mol per mol of transition metal compound.

17. Process according to claim 1, wherein methyl-2-butene-3-nitrile that is present in the reaction mixture obtained from the hydrocyanation of butadiene is isomerized into pentene nitriles in the absence of hydrogen cyanide by operating in the presence of a catalyst that comprises a compound comprising at least one furylphosphine of formula (I) or (II) and at least one transition metal.

18. Process according to claim 17, wherein the methyl-2-butene-3-nitrile that is subjected to the isomerization is used alone or in a mixture with methyl-2-butene-2-nitrile, pentene-4-nitrile, pentene-3-nitrile, pentene-2-nitrile, butadiene, adiponitrile, methyl-2-glutaroronitrile, ethyl-2-succinonitrile or valeronitrile.

19. Process according to claim 17, wherein the isomerization reaction is carried out at a temperature of 10° C. to 200° C.

20. Process according to claim 17, wherein the isomerization into pentene nitriles of methyl-2-butene-3-nitrile is carried out in the presence of at least one compound of a transition metal, at least one furylphosphine of formula (I) or (II) and a co-catalyst that comprises at least one Lewis acid.

* * * * *